United States Patent [19]

Mueller

[11] Patent Number: 4,681,939
[45] Date of Patent: Jul. 21, 1987

[54] 8-CHLORODIBENZ[B,F][1,4]OXAZEPINE-10-(11H)-CARBOXYLIC ACID, 2-[(PHENYLTHIO)ALKANOYL]HYDRAZIDES

[75] Inventor: Richard A. Mueller, Glencoe, Ill.

[73] Assignee: G. D. Searle & Co., Skokie, Ill.

[21] Appl. No.: 931,369

[22] Filed: Nov. 14, 1986

Related U.S. Application Data

[62] Division of Ser. No. 770,457, Aug. 29, 1985.

[51] Int. Cl.[4] .......................................... C07D 267/20
[52] U.S. Cl. .................................................. 540/547
[58] Field of Search ...................................... 540/547

[56] References Cited

U.S. PATENT DOCUMENTS

| | | | |
|---|---|---|---|
| 3,534,019 | 10/1970 | Coyne et al. | 540/547 |
| 3,917,649 | 11/1975 | Mueller | 540/547 |
| 3,989,719 | 11/1976 | Mueller | 540/547 |
| 3,992,375 | 11/1976 | Mueller | 540/547 |
| 4,045,442 | 8/1977 | Mueller | 540/547 |
| 4,125,532 | 11/1978 | Mueller | 540/547 |
| 4,170,593 | 10/1979 | Mueller | 540/547 |

Primary Examiner—Norma S. Milestone
Attorney, Agent, or Firm—J. T. Keane; P. D. Matukaitis; R. E. Henderson

[57] ABSTRACT

This invention relates to 8-chlorodibenz[b,f][1,4]oxazepine-10(11H)-carboxylic acid, 2-[(substituted phenylsulfinyl)alkanoyl]hydrazides and 8-chlorodibenz[b,f][1,4]oxazepine-10(11H)-carboxylic acid, 2-[(substituted phenylsulfonyl)alkanoyl]hydrazides that are useful as prostaglandin antagonists and analgesic agents. This invention also relates to 8-chlorodibenz[b,f][1,4]oxazepine-10(11H)-carboxylic acid, 2-[(substituted phenylthio)alkanoyl]hydrazides that are useful as intermediates in the preparation of the corresponding sulfinyl and sulfonyl compounds.

2 Claims, No Drawings

8-CHLORODIBENZ[B,F][1,4]OXAZEPINE-10-(11H)-CARBOXYLIC ACID, 2-[(PHENYLTHIO)ALKANOYL]HYDRAZIDES

This is a division of application Ser. No 770,457, filed Aug. 29, 1985.

BACKGROUND OF THE INVENTION (a) Field of the Invention

This invention relates to 8-chlorodibenz[b,f][1,4]oxazepine-10(11H)-carboxylic acid, 2-[(substituted phenylsulfinyl)alkanoyl]hydrazides and 8-chlorodibenz[b,f][1,4]oxazepine-10(11H)-carboxylic acid, 2-[(substituted phenylsulfonyl)alkanoyl]hydrazides that are useful as pharmacologic agents. These compounds are prostaglandin antagonists having analgesic activity. This invention also relates to 8-chlorodibenz[b,f][1,4]oxazepine-10(11H)-carboxylic acid, 2-[(substituted phenylthio)alkanoyl]hydrazides that are useful as intermediates in the preparation of the corresponding sulfinyl and sulfonyl compounds.

Analgesics are agents used in the treatment of pain and often are useful in alleviating inflammation. The major classes of analgesics include narcotic analgesics (or opiates) and analgesic-antipyretics such as the salicylates. Although the efficacy of opiates in relieving pain is well-established, the associated addiction liability is a distinct disadvantage. Although salicylate and salicylate-like agents (non-steroidal antiinflammatory agents) are also efficacious in relieving pain, they often exhibit undesirable side effects such as gastrointestinal irritation (as with aspirin), allergic response (as with aspirin), or liver toxicity with extended use (as with acetaminophen). The compounds included in this invention are neither opiates nor salicylates and may be expected not to exhibit the disadvantages of either class of compound.

(b) Prior Art

Related 8-chlorodibenz[b,f][1,4]oxazepine-10(11H)-carboxylic acid, 2-(sulfinyl- and sulfonyl-containing acyl)hydrazides have been disclosed in a copending application, now U.S. Pat. No. 4,559,336, and related 8-chlorodibenz[b,f][1,4]oxazepine-10(11H)-carboxylic acid, 2-(alkoxy-containing acyl)hydrazides have been disclosed in a copending application, now U.S. Pat. No. 4,559,337, both patents having the same assignee as the present application. Compounds in U.S. Pat. Nos. '336 and '337 are also prostaglandin antagonists having analgesic activity but differ from compounds of the present application in the composition of the acyl side chains.

The closest perior art discloses compounds of the following formula, wherein group B is carbonyl (CO) or sulfonyl ($SO_2$) and A may be alkyl or substituted alkyl. The prior art does not, however, disclose nor anticipate the compounds of this invention.

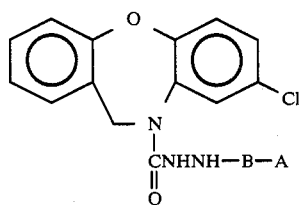

More specifically, U.S. Pat. No. 3,534,019 discloses compounds in which B and A together constitute "lower alkanoyl," and U.S. Pat. No. 3,989,719 discloses compounds in which B and A together constitute "higher alkanoyl." Japanese Patent Application No. 128955/75 discloses compounds in which B is carbonyl and A is alkenyl, phenylalkenyl, and (cycloalkyl)alkyl. Thus, U.S. Pat. Nos. '019 and '719 and the Japanese application each disclose compounds in which A is a hydrocarbon. The thio-, sulfoxide-, and sulfone-containing compounds of this invention are not disclosed.

U.S. Pat. Nos. 4,045,442, 4,125,532 (division of '442), and 4,170,593 (division of '532) disclose compounds in which B is carbonyl and A is (substituted amino)alkyl. The sulfur-containing compounds of this invention are not disclosed.

U.S. Pat. Nos. 3,917,649 and 3,992,375 (division of '649) disclose compounds in which B is carbonyl or sulfonyl: where B is carbonyl, A may be haloalkyl, alkenyl, or aryloxyalkyl; and where B is sulfonyl, A may be alkyl, haloalkyl, aryl, or aralkyl. U.S. Pat. Nos. '649 and '375 thus disclose compounds in which a sulfonyl group must be attached directly to a hydrazine nitrogen, but do not disclose compounds in which B is carbonyl and A contains thio, sulfoxide, or sulfone groups. Thus, the compounds of this invention are structurally distinct from the prior art.

SUMMARY OF THE INVENTION

This invention relates to compounds of Formula I:

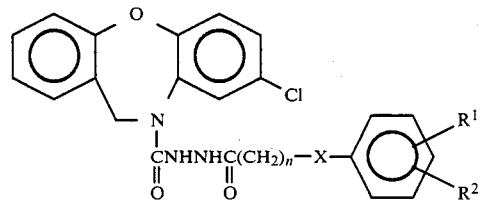

wherein X is S, SO, or $SO_2$;
wherein
$R^1$ is:
 (a) hydrogen;
 (b) alkyl of 1 to 4 carbon atoms, inclusive;
 (c) alkoxy of 1 to 4 carbon atoms, inclusive; or
 (d) halogen;
wherein
$R^2$ is:
 (a) hydrogen;
 (b) alkyl of 1 to 4 carbon atoms, inclusive;
 (c) alkoxy of 1 to 4 carbon atoms, inclusive; or
 (d) halogen; and
wherein
n is an integer from 1 to 4, inclusive.

Examples of alkyl of 1 to 4 carbon atoms, inclusive, are methyl, ethyl, propyl, butyl, and the isomeric forms thereof, generally referred to as lower alkyl.

Examples of alkoxy of 1 to 4 carbon atoms, inclusive, are methoxy, ethoxy, propoxy, butoxy, and the isomeric forms thereof.

Examples of halogen are fluorine, chlorine, bromine, and iodine.

DESCRIPTION OF THE INVENTION

The compounds of this invention may be prepared by the methods illustrated in the following Schemes. Unless otherwise specified, the various substituents are defined as for Formula I, above. Scheme A illustrates the preparation of thio compounds of this invention, Formula IV (Formula I in which X is S).

SCHEME A

Compounds of Formula IV are prepared from 8-chloro-10,11-dihydrodibenz[b,f][1,4]oxazepine-10-carboxylic acid hydrazide (Formula II), the preparation of which is described in U.S. Pat. No. 3,534,019, by at least two different routes. In the first route, described in U.S. Pat. No. 4,045,442, the hydrazide of Formula II is acylated to give an intermediate of Formula III. The preferred group Y is a chlorine atom.

An intermediate of Formula III may be converted to a compound of Formula IV by any of several methods. For example, a preferred method involves direct reaction of an optionally substituted thiophenol with the intermediate of Formula III in the presence of a base, such as a tertiary amine.

In a second route used to prepare compounds of Formula IV, the hydrazide of Formula II is acylated with an appropriate acyl halide of Formula V in the presence of a base. Preferred acylating conditions include reaction of the hydrazide (Formula II) and an acyl chloride (Formula V, Z=Cl) in an unreactive organic solvent, such as dichloromethane, containing a tertiary amine, such as triethylamine. The acyl halides may be prepared from the corresponding carboxylic acids by methods well known to those skilled in the art.

Scheme B illustrates the preparation of sulfoxides of this invention, Formula VI (Formula I in which X is SO), and sulfones of this invention, Formula VII (Formula I in which X is $SO_2$).

SCHEME B

Compounds of Formulas VI and VII are each prepared by oxidizing intermediates of Formula IV, preferably using a peroxycarboxylic acid in a cooled solvent. Careful control of the oxidizing conditions permits preparing sulfoxides VI without significant further oxidation to sulfones VII. Preferred conditions for preparing sulfoxides VI include oxidizing intermediates IV with an approximately equimolar quantity of m-chloroperoxybenzoic acid in an organic solvent, such as dichloromethane, at about 0°. Oxidization is then quenched by adding aqueous sodium thiosulfate.

Sulfones VII may be prepared by two general methods. First, intermediates IV may be oxidized directly to sulfones VII. Preferred conditions for such a direct oxidation are similar to those described above for the corresponding sulfoxides VI, except that a two-fold molar quantity of m-chloroperoxybenzoic acid is used. Oxidization is similarly quenched by adding aqueous sodium thiosulfate. Second, sulfoxides VI may be oxidized to sulfones VII. Preferred conditions for such an oxidation are essentially identical to those used to form sulfoxides VI from intermediates IV.

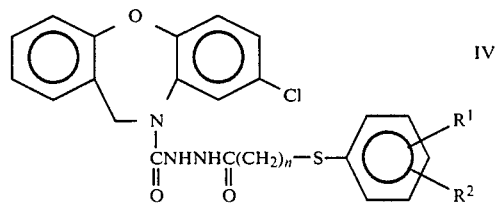

-continued
SCHEME B

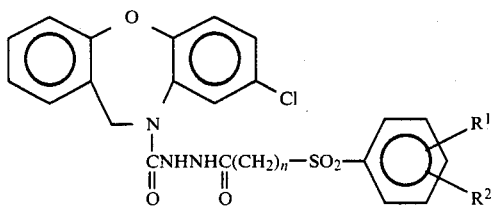

VII

The preferred embodiments of this invention, as indicated by biological activity in the following assays, are compounds according to Formula I wherein X is $SO_2$. The most preferred embodiment of this invention is a compound according to Formula I wherein X is $SO_2$, $R^1$ and $R^2$ are each hydrogen, and n is 1 (exemplified in Example 3 below).

The compounds are prostaglandin $E_2$ antagonists, as indicated by the guinea pig ileum assay performed essentially as described by J. H. Sanner, *Arch. int. Pharmacodyn*, 180, 46 (1969). The compounds of this invention exhibit analgesic activity in mice, as indicated by the PBQ-writhing assay. The activities of the compounds of this invention illustrated in the examples were determined by the following methods.

PROSTAGLANDIN ANTAGONISM ASSAY

Female albino guinea pigs weighing 200 to 500 grams were sacrificed by cervical dislocation. The ileum was quickly removed and placed in a modified Tyrode solution containing one-half the usual amount of magnesium ions. Segments of ileum about 2 cm long were cut and mounted in a 2- or 4-ml tissue bath containing the modified Tyrode solution, and the solution was maintained at 37° and aerated with a gaseous mixture of 95% oxygen and 5% carbon dioxide. Contractions were detected isotonically. Submaximal contractions were obtained by adjusting the dose of prostaglandin $E_2$ ($PGE_2$) added to the bath. Two control contractions were obtained at 3.5 minute intervals. A solution or suspension of the test compound in the bathing solution was then substituted for the original modified Tyrode solution. The test suspension was kept in constant contact with the tissue for the remainder of the experiment, except for brief periods to drain the bath in preparation for rinsing with fresh test suspension. Three more contractions were elicited for the $PGE_2$ agonist in the presence of the test compound without interrupting the time sequence. The last two sets of treated responses were compared with the two sets of control responses. (The first set of treated responses was not used for comparisons, being used only to maintain the timed sequence of injections during the period allowed for the tissue to become equilibrated with the antagonist.) A compound was rated active if the mean of contractions produced by the agonist was reduced 75% or more by the test compound.

PBQ-WRITHING ASSAY

Male Charles River albino mice (CD-1(ICR)BR) weighing 20 to 30 grams were used in this assay. Thirty minutes after subcutaneous or intragastric administration (0.1 ml per 10 g of body weight) or fifteen minutes after intracerebroventricular administration (5 mcl total volume), a 0.025% solution of phenylbenzoquinone (PBQ) was injected intraperitoneally (0.1 ml per 10 g of body weight). Five minutes later each mouse was placed in a glass beaker and the number of writhes occurring in the next ten minutes was counted. (A writhe consists of dorsoflexion of the back, extension of the hindlimbs, and strong contraction of the abdominal musculature.) The test compound was considered to have produced analgesia in a mouse if the number of writhes elicited by PBQ was equal to or less than one-half the median number of writhes recorded for the saline-treated control group of mice that day. Results were expressed as the number of mice out of a possible ten in which the test compound produced analgesia. If the initial screening dose of 10 mg/kg inhibited writhing in greater than six of ten mice, the effect of additional doses of the compound on the writhing response was evaluated and an $ED_{50}$ was calculated.

By virtue of their analgesic activity, the sulfinyl and sulfonyl compounds of Formula I are useful in treating pain in mammals. A physician or veterinarian of ordinary skill can readily determine whether a subject is in pain. Regardless of the route of administration selected, the compounds of the present invention are formulated into pharmaceutically acceptable dosage forms by conventional methods known to those skilled in the art. Moreover, the compounds may be used in a suitable hydrated form.

The compounds can be administered in such oral dosage forms as tablets, capsules, pills, powders, granules, elixirs, or syrups. They may also be administered intravascularly, intraperitoneally, subcutaneously, intramuscularly, or topically, using forms known to the pharmaceutical art. In general, the preferred form of administration is oral. An effective but non-toxic quantity of the compound is employed in treatment. The dosage regimen for treating pain with the compounds of this invention is selected in accordance with a variety of factors, including the type, age, weight, sex, and medical condition of the patient; the severity of the pain; the route of administration; and the particular compound employed. An ordinarily skilled physician or veterinarian can readily determine and prescribe the effective amount of the drug required to prevent or arrest the progress of the condition. In so proceeding, the physician or veterinarian could employ relatively low doses at first and subsequently increase the dose until a maximum response is obtained. Dosages of the sulfinyl and sulfonyl compounds of the invention may be in the range of 0.1 to 100 mg/kg, preferably in the range of about 0.5 to 5.0 mg/kg.

In the pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate, mannitol, and the like; for oral administration in liquid form, the active drug components may be combined with any oral non-toxic pharmaceutically acceptable inert carrier such as ethanol and the like. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like. Sweetening and flavoring agents and preservatives can also be included where appropriate.

The following examples further illustrate details for the preparation of the compounds of this invention. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted.

DESCRIPTION OF THE EMBODIMENTS

EXAMPLE 1

(phenylthio)acetyl chloride

To a solution of 5.0 g of (phenylthio)acetic acid in 20 ml of toluene under nitrogen was added 5.2 ml of oxalyl chloride in four portions. The solution was stirred at room temperature for about twenty hours and then concentrated in vacuo to the oily title compound, which was used in subsequent reactions without further purification or characterization.

EXAMPLE 2

8-chlorodibenz[b,f][1,4]oxazepine-10(11H)-carboxylic acid, 2-[(phenylthio)acetyl]hydrazide

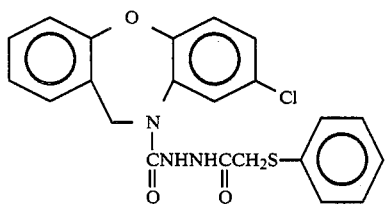

To a stirred mixture of 5.89 g of 8-chloro-10,11-dihydrodibenz[b,f][1,4]oxazepine-10-carboxylic acid hydrazide (see U.S. Pat. No. 3,534,019) and 2.8 ml of triethylamine in 50 ml of cold (ca. 0°) dichloromethane was slowly added 3.8 g of the title product of Example 1. The mixture was then stirred for twenty hours at room temperature. The solution was then washed three times with 50-ml portions of water, dried over sodium sulfate, filtered, and concentrated in vacuo to give the title compound, m.p. 172°–175°.

Analysis. Calcd. for $C_{22}H_{18}N_3O_3SCl$: C, 60.07; H, 4.12; N, 9.55; S, 7.29; Cl, 8.06. Found: C, 59.87; H, 4.17; N, 9.76.

EXAMPLE 3

8-chlorodibenz[b,f][1,4]oxazepine-10(11H)-carboxylic acid, 2-[(phenylsulfonyl)acetyl]hydrazide

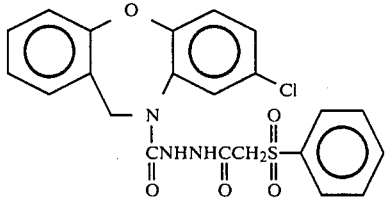

To a stirred solution of 2.0 g (4.5 mmole) of the title product of Example 2 in 40 ml of cold (ca. 0°) dichloromethane was added 1.94 g (9.1 mmole) of 81% m-chloroperoxybenzoic acid. After about ninety minutes, 10 ml of saturated aqueous sodium thiosulfate was added. The mixture was washed sequentially with three portions of saturated aqueous sodium bicarbonate and three portions of water. The organic phase was dried over sodium sulfate, filtered, and concentrated in vacuo to give the title compound, m.p. 180°–183°.

Analysis. Calcd. for $C_{22}H_{18}N_3O_5SCl$: C, 55.99; H, 3.84; N, 8.90; S, 6.79; Cl, 7.51. Found: C, 56.00; H, 3.73; N, 8.85; S, 6.80.

EXAMPLE 4

8-chlorodibenz[b,f][1,4]oxazepine-10(11H)-carboxylic acid, 2-[(phenylsulfinyl)acetyl]hydrazide

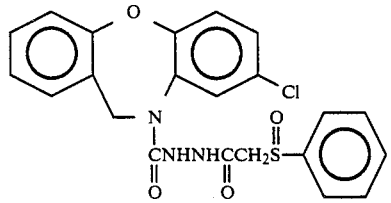

To a stirred solution of 1.0 g (2.19 mmole) of the title product of Example 2 in 30 ml of cold (ca. 0°) dichloromethane was added 0.463 g (2.19 mmole) of 81% m-chloroperoxybenzoic acid. After about ninety minutes, 5 ml of saturated aqueous sodium thiosulfate was added. The mixture was washed sequentially with three portions of saturated aqueous sodium bicarbonate and three portions of water. The organic phase was dried over sodium sulfate, filtered, and concentrated in vacuo to give tht title compound.

What is claimed is:

1. A compound of the formula:

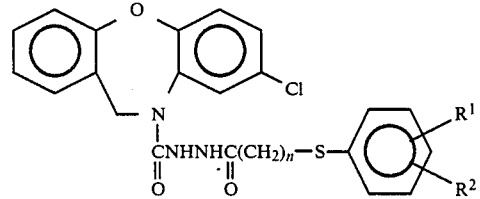

wherein
R1 is:
(a) hydrogen;
(b) alkyl of 1 to 4 carbon atoms, inclusive;
(c) alkoxy of 1 to 4 carbon atoms inclusive or
(d) halogen;
wherein
R² is:
(a) hydrogen;
(b) alkyl of 1 to 4 carbon atoms, inclusive;
(c) alkoxy of 1 to 4 carbon atoms, inclusive; or
(d) halogen; and
wherein
n is an integer from 1 to 4 inclusive.

2. A compound according to claim 1, which is 8-chlorodibenz[b,f][1,4]oxazepine-10(11H)-carboxylic acid, 2-[(phenylthio)acetyl]hydrazide.